United States Patent
Quill et al.

(10) Patent No.: US 11,826,250 B2
(45) Date of Patent: *Nov. 28, 2023

(54) TRANSCATHETER VALVE PROSTHESIS DELIVERY SYSTEM WITH RECAPTURING FEATURE AND METHOD

(71) Applicant: Medtronic, Inc., Minneapolis, MN (US)

(72) Inventors: Jason Quill, Forest Lake, MN (US); Paul Rothstein, Elk River, MN (US); Thomas Secord, Mounds View, MN (US); Byron Johnson, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 325 days.

This patent is subject to a terminal disclaimer.

(21) Appl. No.: 16/924,328

(22) Filed: Jul. 9, 2020

(65) Prior Publication Data
US 2020/0337839 A1 Oct. 29, 2020

Related U.S. Application Data

(60) Continuation of application No. 15/591,501, filed on May 10, 2017, now Pat. No. 10,743,989, which is a
(Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/9517* (2020.05); *A61F 2250/0093* (2013.01)

(58) Field of Classification Search
CPC ...... A61F 2/2427; A61F 2/243; A61F 2/2433; A61F 2/2436; A61F 2/2439;
(Continued)

(56) References Cited

U.S. PATENT DOCUMENTS 4,729,373 A * 3/1988 Peyman .............. A61F 9/00821
606/4
5,951,566 A 9/1999 Lev
(Continued)

FOREIGN PATENT DOCUMENTS

EP 0832616 4/1998
WO WO2010/014515 2/2010

OTHER PUBLICATIONS

PCT/US2013/067878 PCT Search Report and Written Opinion, dated Feb. 21, 2014.
(Continued)

*Primary Examiner* — Diane D Yabut
*Assistant Examiner* — Christian D. Knauss
(74) *Attorney, Agent, or Firm* — Medler Ferro Woodhouse & Mills PLLC

(57) ABSTRACT

A delivery system for percutaneously deploying a valve prosthesis. The system includes a catheter assembly including a delivery sheath capsule and a handle having an oscillating device. The capsule is configured to compressively retain the valve prosthesis during implantation. After the valve prosthesis is partially exposed during implantation, the oscillating device can create a vibratory motion to reduce the friction between the valve prosthesis and the delivery sheath capsule in order to recapture the valve prosthesis.

20 Claims, 4 Drawing Sheets

Related U.S. Application Data division of application No. 13/668,085, filed on Nov. 2, 2012, now Pat. No. 9,675,456.

(58) Field of Classification Search
CPC .......... A61F 2/2466; A61F 2/95; A61F 2/962; A61F 2/966; A61F 2/97; A61F 2002/9517; A61F 2002/9534; A61F 2002/9583

See application file for complete search history.

(56) References Cited

U.S. PATENT DOCUMENTS

| | | | |
|---|---|---|---|
| 6,346,091 B1 | 2/2002 | Jacobsen et al. | |
| 6,375,615 B1 | 4/2002 | Flaherty et al. | |
| 6,562,032 B1 | 5/2003 | Ellman et al. | |
| 6,660,024 B1 | 12/2003 | Flaherty et al. | |
| 7,637,870 B2 | 12/2009 | Flaherty et al. | |
| 7,803,168 B2 | 9/2010 | Gifford et al. | |
| 8,123,774 B2 | 2/2012 | Mamayek et al. | |
| 10,743,989 B2 * | 8/2020 | Quill | A61F 2/2436 |
| 2002/0177889 A1 | 11/2002 | Brisken et al. | |
| 2002/0188243 A1 | 12/2002 | Brisken et al. | |
| 2003/0078651 A1 | 4/2003 | Schoon et al. | |
| 2003/0204237 A1 * | 10/2003 | Krivoruchko | A61B 17/22 623/1.11 |
| 2004/0010304 A1 | 1/2004 | Weber et al. | |
| 2004/0181236 A1 * | 9/2004 | Eidenschink | A61F 2/9524 623/901 |
| 2004/0186464 A1 | 9/2004 | Mamayek et al. | |
| 2005/0209669 A1 | 9/2005 | Kao | |
| 2006/0265056 A1 | 11/2006 | Nguyen et al. | |
| 2007/0173861 A1 | 7/2007 | Strommer et al. | |
| 2007/0239266 A1 | 10/2007 | Birdsall | |
| 2007/0239269 A1 | 10/2007 | Dolan et al. | |
| 2008/0288043 A1 | 11/2008 | Kaufmann et al. | |
| 2008/0294230 A1 | 11/2008 | Parker | |
| 2009/0254165 A1 | 10/2009 | Tabor et al. | |
| 2010/0049313 A1 | 2/2010 | Alon et al. | |
| 2011/0098804 A1 | 4/2011 | Yeung et al. | |
| 2011/0118634 A1 | 5/2011 | Golan | |
| 2011/0224596 A1 | 9/2011 | Flaherty et al. | |
| 2011/0251676 A1 | 10/2011 | Sweeney et al. | |
| 2011/0251681 A1 * | 10/2011 | Shipley | A61F 2/2418 623/2.11 |
| 2011/0264199 A1 | 10/2011 | Tran et al. | |
| 2012/0239142 A1 | 9/2012 | Liu et al. | |
| 2013/0152658 A1 * | 6/2013 | Davis | A61F 2/95 72/402 |

OTHER PUBLICATIONS

Communication Pursuanto Article 94(3) EPC, European Application No. 13795621.5, dated Dec. 22, 2021.

* cited by examiner

TRANSCATHETER VALVE PROSTHESIS DELIVERY SYSTEM WITH RECAPTURING FEATURE AND METHOD

RELATED APPLICATIONS

This application is a Continuation of U.S. patent application Ser. No. 15/591,501, filed May 10, 2017, which is a Continuation of U.S. patent application Ser. No. 13/668,085, filed Nov. 2, 2012, now U.S. Pat. No. 9,675,456, the disclosures of each of which are herein incorporated by reference in their entirety.

BACKGROUND OF THE INVENTION

Field of the Invention

The present invention is related to systems and methods for percutaneous implantation of a heart valve prosthesis.

Background Art

Cardiac valves exhibit two types of pathologies: regurgitation and stenosis. Regurgitation is the more common of the two defects. Either defect can be treated by a surgical repair.

Under certain conditions, the cardiac valve must be replaced. Standard approaches to valve replacement require cutting open the patient's chest and heart to access the native valve. Such procedures are traumatic to the patient, require a long recovery time, and can result in life threatening complications. Therefore, many patients requiring cardiac valve replacement are deemed to pose too high a risk for open heart surgery due to age, health, or a variety of other factors. These patient risks associated with heart valve replacement are lessened by the emerging techniques for minimally invasive valve repair, but still many of those techniques require arresting the heart and passing the blood through a heart-lung machine.

Efforts have been focused on percutaneous transluminal delivery of replacement cardiac valves to solve the problems presented by traditional open heart surgery and minimally-invasive surgical methods. In such methods, a valve prosthesis is compacted for delivery in a catheter and then advanced, for example, through an opening in the femoral artery and through the descending aorta to the heart, where the prosthesis is then deployed in the aortic valve annulus.

Various types and configurations of valve prostheses are available for percutaneous valve replacement procedures, and continue to be refined. The actual shape and configuration of any particular valve prosthesis is dependent to some extent upon the native shape and size of the valve being repaired (i.e., mitral valve, tricuspid valve, aortic valve, or pulmonary valve). In general, valve prosthesis designs attempt to replicate the functions of the valve being replaced and thus will include valve leaflet-like structures. A typical percutaneous valve prosthesis includes a replacement valve that is mounted in some manner within an expandable stent frame to make a valved stent (or "valve prosthesis"). For many percutaneous delivery and implantation devices, the stent frame of the valved stent is made of a self-expanding material and construction. With these devices, the valved stent is crimped down to a desired size and held in that compressed arrangement within an outer sheath, also known as a capsule, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. Once delivered to the implantation site, the balloon is inflated to deploy the prosthesis. With either of these types of percutaneous stented valve prosthesis delivery devices, conventional sewing of the valve prosthesis to the patient's native tissue is typically not necessary.

It is imperative that the stented valve prosthesis be accurately located relative to the native annulus immediately prior to full deployment from the catheter as successful implantation requires the valve prosthesis intimately lodge and seal against the native annulus. If the prosthesis is incorrectly positioned relative to the native annulus, serious complications can result as the deployed device can leak and can even dislodge from the native valve implantation site.

While imaging technology can be employed as part of the implantation procedure to assist a clinician in better evaluating a location of the transcatheter valve prosthesis immediately prior to deployment, in many instances, this evaluation alone is insufficient. Instead, clinicians desire the ability to partially deploy the prosthesis, evaluate a position relative to the native annulus, and then reposition the prosthesis prior to full deployment if deemed necessary. Repositioning, in turn, requires the prosthesis first be re-compressed and re-located back within the outer delivery sheath. Stated otherwise, the partially deployed stented valve prosthesis must be "recaptured" by the delivery device, and in particular within the outer sheath. While, in theory, the recapturing of a partially deployed stented valve prosthesis is straight forward, in actual practice, the constraints presented by the implantation site and the stented heart valve itself render the technique exceedingly difficult.

For a self-expanding device, the stented heart valve is submerged in cold water in order to attach the stented heart valve onto the delivery system. This is because the shape memory material, typically Nitinol, is flexible at low temperatures. At warmer temperatures, for example inside the human body, the shape memory material becomes more rigid. In short, the stented heart valve is purposefully designed to rigidly resist collapsing forces once deployed to properly anchor itself in the anatomy of the heart. Thus, the delivery device component (e.g., outer delivery sheath) employed to force a partially-deployed segment of the prosthesis back to a collapsed arrangement must be capable of exerting a significant radial force. Conversely, however, the component cannot be overly rigid so as to avoid damaging the transcatheter heart valve as part of a recapturing procedure. Along these same lines, the aortic arch must be traversed, necessitating that the delivery device provide sufficient articulation attributes.

As mentioned above, an outer sheath or catheter is conventionally employed to deliver a self-deploying vascular stent. For the delivery of a self-deploying stented valve prosthesis, the high radial expansion force associated with the prosthesis is not problematic for complete deployment as the outer sheath is simply retracted in tension to allow the valve prosthesis to deploy. Were the conventional delivery device operated to only partially withdraw the outer sheath relative to the prosthesis, only the so-exposed distal region of the prosthetic would expand while the proximal region remained coupled to the delivery device. In theory, the outer sheath could simply be advanced distally to recapture the expanded region. Unfortunately, with conventional sheath configurations, attempting to compress the expanded region of the stented valve prosthesis by distally sliding the sheath is unlikely to be successful. The conventional delivery sheath cannot readily overcome the radial force of the expanded region of the prosthesis because, in effect, the sheath is placed into compression and will collapse due at least in part to the abrupt edge of the sheath being unable to cleanly slide over the expanded region of the prosthesis.

BRIEF SUMMARY OF THE INVENTION

Provided herein is a valve prostheses delivery system that generally includes a delivery system having a handle at a proximal end and a capsule at a distal end. The capsule surrounds a compressed valve prosthesis for delivery through a patient's vasculature. The handle includes an oscillating device that induces a vibratory motion on the delivery system. Such a configuration achieves numerous goals. For example, such a configuration allows for a reduction in the friction coefficient between the outer surface of the valve prosthesis and the inner surface of the capsule during recapture of the valve prosthesis. This configuration also allows for a reduction in the axial force required to recapture the valve prosthesis.

In view thereof, disclosed herein are aspects of a delivery device including a sheath and an oscillator configured to transmit vibratory motion to a sheath at a defined frequency.

In another exemplary embodiment, disclosed herein are aspects of a delivery system including a sheath and an ultrasonic device configured to transmit ultrasonic energy at a defined frequency to the sheath to induce a vibratory motion.

In another exemplary embodiment, disclosed herein are aspects of a method of treating a valve disorder in a patient's heart including delivering a compressed valve prosthesis attached to a delivery device to an implantation site, the delivery device including a capsule that compressively contains the valve prosthesis, and proximately retracting the capsule relative to the compressed valve prosthesis to expose a region of the valve prosthesis such that the exposed region expands to an uncompressed state, applying a vibration to the capsule and proximally advancing the valve prosthesis relative to the delivery device to cause the exposed region of the valve prosthesis to transition toward a compressed arrangement within an interior area of the capsule, and proximately retracting the capsule relative to the compressed valve prosthesis to deploy the valve prosthesis at the implantation site.

BRIEF DESCRIPTION OF THE DRAWINGS/FIGURES

The accompanying figures, which are incorporated herein, form part of the specification and illustrate embodiments of a valve prosthesis delivery system. Together with the description, the figures further serve to explain the principles of and to enable a person skilled in the relevant art(s) to make, use, and implant a valve prosthesis using the valve prosthesis delivery system described herein. In the drawings, like reference numbers indicate identical or functionally similar elements.

DETAILED DESCRIPTION OF THE INVENTION

Figure 1:
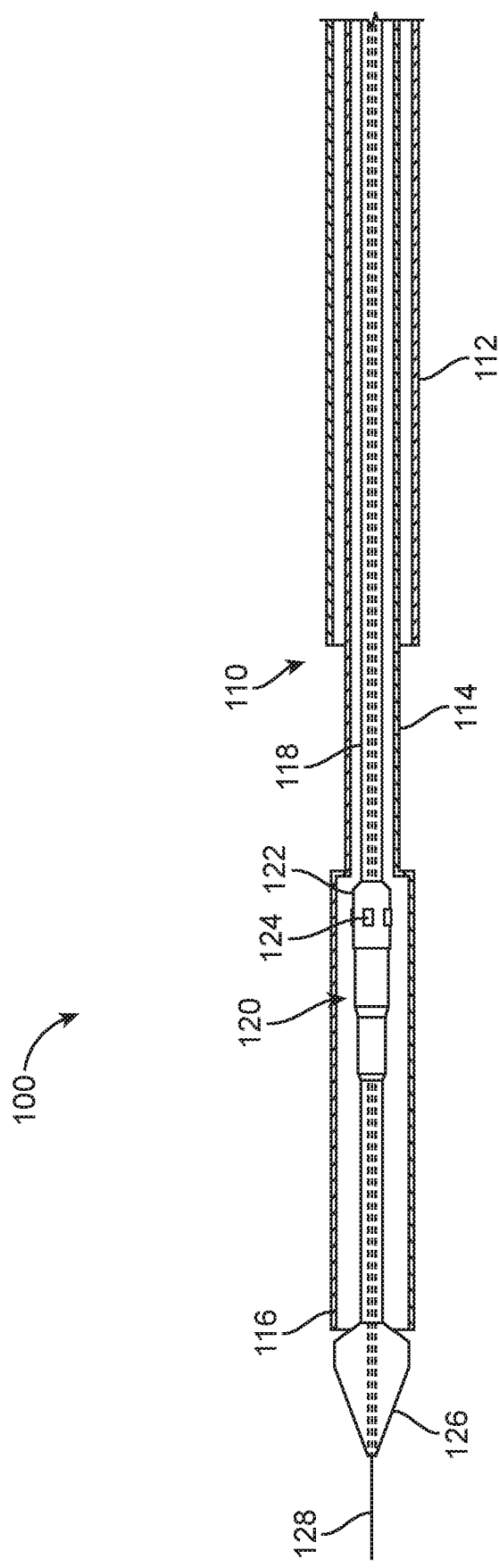
FIG. 1 is a sectional view of a valve prosthesis delivery system according to an aspect of this disclosure.
Figure 2:
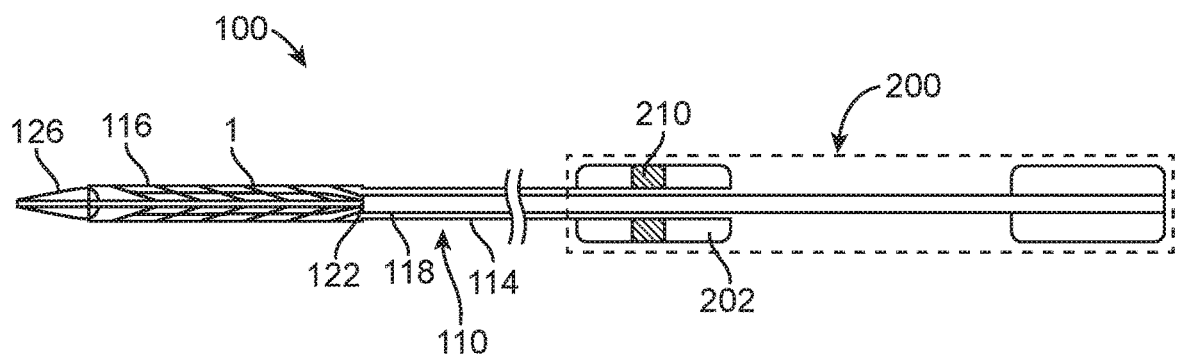
FIG. 2 is a simplified sectional view of a valve prosthesis delivery system according to an aspect of this disclosure.

The following detailed description of a valve prosthesis delivery system refers to the accompanying figures that illustrate exemplary embodiments. Other embodiments are possible. Modifications can be made to the embodiments described herein without departing from the spirit and scope of the present invention. Therefore, the following detailed description is not meant to be limiting.

The present invention is directed to a heart valve prosthesis delivery system including an oscillating device to transmit vibratory motion along the delivery system. The vibratory motion can be used to reduce friction between surfaces, which is commonly known as applying a "dither." Friction of two objects in vibration can reduce the friction coefficient and friction forces between the two objects, lighten the abrasion between the objects, reduce energy consumption, and greatly increase working efficiency. In the present invention, the recapture forces in the delivery system are reduced by applying a vibration between the inner surface of the delivery system capsule, which houses the valve prosthesis during delivery, and the outer surface of the valve frame. In a further aspect of the invention, the vibration can create a coordinated traveling wave within the delivery system capsule structure thus making the recapture process peristaltic.

The delivery system delivers a valve prosthesis percutaneously to the heart to replace the function of a native valve. For example, the valve prosthesis can replace a bicuspid or a tricuspid valve such as the aortic, mitral, pulmonary, or tricuspid heart valve. The valve can be delivered, for example, transfemorally, transeptally, transapically, transradially, transsubclavian, or transatrially.

Valve prostheses typically have a coupling feature to attach the valve prostheses to a delivery system. The coupling feature typically attaches to a corresponding feature on the delivery system which retains the valve prosthesis. In addition, valve prosthesis delivery systems typically include a sheath, referred to herein as a sheath or capsule, that surrounds the collapsed valve prosthesis during delivery to the implantation site. During deployment, the capsule is withdrawn over the valve prosthesis.

Referring now to FIGS. 1-6, the delivery system for valve prosthesis 1 includes catheter assembly 110 that includes an outer sheath 112, a pusher tube 114, and a central tube 118, each of which are concentrically aligned and permit relative motion with respect to each other. Catheter assembly 110 also includes a guidewire lumen provided for guidewire 128. At a distal end of pusher tube 114 is a capsule 116. At a distal end of central tube 118 is plunger assembly 120. Capsule 116 surrounds plunger assembly 120 and collapsed valve prosthesis 1 during delivery of valve prosthesis 1. Plunger assembly 120 includes hub 122 at a proximal end and tip 126 at a distal end. Tip 126 facilitates the advancement of catheter assembly 110 through the patient's vasculature. Hub 122 includes attachments 124 (referenced generally) configured to selectively capture a corresponding attachment feature of the valve prosthesis. Attachments 124 can assume various forms. In one aspect, attachments 124 are geometric tabs sized to receive a corresponding component(s) of the valve prosthesis. In an alternate aspect, attachments 124 form one or more slots sized to slidably receive a corresponding component(s) of the valve prosthesis (e.g., a bar or leg segment of the stent frame). Further, the plunger assembly 120 can incorporate additional structures and/or mechanisms that assist in temporarily retaining the stented valve (e.g., a tubular sleeve biased over the hub 122). A non-limiting example of a plunger assembly useful with the present disclosure is described in U.S. application Ser. No. 12/870,567 entitled "Transcatheter Valve Delivery Systems and Methods" filed Aug. 27, 2010, which is incorporated herein by reference in its entirety. Other releasable coupling arrangements are also acceptable, such as hub 122 including one or more fingers sized to be received within corresponding apertures formed by the valve prosthesis stent frame (e.g., the valve prosthesis stent frame can form wire loops at a proximal end thereof that are received over respective ones of the fingers when compressed within capsule 116).

In one aspect of the invention, a shape memory (e.g., Nitinol) structure is incorporated into capsule 116. This allows a portion of capsule 116 to expand circumferentially or flare at a distal end thereof when encountering the outward radial forces (or resistance to radial compression) of the transcatheter valve prosthesis 1 during deployment and recapture. The expanded structure reduces the peak forces required to collapse the cells of a stent frame of valve prosthesis 1 by redistributing the potential energy along a length of the expanded flare. One non-limiting example of a flared delivery system capsule useful with the present disclosure is described in U.S. Patent Publication No. 2011/0251681, which is incorporated herein by reference in its entirety.

In general terms, the stented valve prostheses of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented valve prosthesis useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, which are incorporated herein by reference in their entirety.

The stents or stent frames are support structures that comprise a number of struts or wire portions arranged relative to each other to provide a desired compressibility and strength to the valve prosthesis. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets can be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as can be accomplished using high-strength nano-manufactured NiTi films produced at Advance BioProsthetic Surfaces (ABPS), for example. The stent frame support structures are generally configured to accommodate at least two (typically three) leaflets; however, stented valve prostheses of the types described herein can incorporate more or less than three leaflets.

Delivery system 100 also includes a valve prosthesis 1 and a handle 200. As shown, valve prosthesis 1 collapsed and loaded onto delivery system 100. Valve prosthesis 1 is crimped onto the plunger assembly 120 such that valve prosthesis 1 engages attachments 124. Capsule 116 compressively contains valve prosthesis 1 in the compressed arrangement. As discussed, capsule 116 is configured to permit partial and complete deployment of valve prosthesis 1 from the loaded state, as well as to recapture valve prosthesis 1 following partial deployment.

Handle 200 includes an actuation portion 202. Actuation portion 202 is coupled to pusher tube 114 and is configured to move pusher tube 114 and capsule 116 relative to central tube 118 and plunger assembly 120. In one aspect of the invention, actuation portion 202 can be moved toward a proximal end of handle 200 in order to move pusher tube 114 and capsule 116 relative to central tube 118 to permit partial or complete deployment of valve prosthesis 1. In a further aspect of the invention, actuation portion 202 can be moved from a proximal end of handle 200 to a distal end of handle 200 in order to move pusher tube 114 and capsule 116 relative to central tube 118 to recapture valve prosthesis 1. Handle 200 also includes an oscillating device 210 to transmit vibratory motion to capsule 116 during recapture of valve prosthesis 1.

To deploy valve prosthesis 1 from delivery system 100, capsule 116 is withdrawn from over valve prosthesis 1, for example by proximally retracting pusher tube 114 and capsule 116 by operating actuation portion 202 toward the proximal end of handle body 204, such that the capsule distal end is proximal to attachments 124. Once capsule 116 is proximal the attachments 124, valve prosthesis 1 is allowed to self-expand to a natural arrangement thereby releasing from delivery system 100.

In some instances, a clinician can desire to only partially deploy valve prosthesis 1 and then evaluate positioning before fully releasing valve prosthesis 1. For example, delivery system 100 loaded with valve prosthesis 1 can be employed as part of a method to repair a damaged heart valve of a patient. Under these circumstances, delivery system 100, in the loaded state, is advanced toward the native heart valve implantation target site, for example in a retrograde approach, through a cut-down to the femoral artery and into the patient's descending aorta. Delivery system 100 is then advanced using tip 126, under fluoroscopic guidance, over the aortic arch, through the ascending aorta, and midway across the defective aortic valve (for aortic valve replacement).

Figure 3:
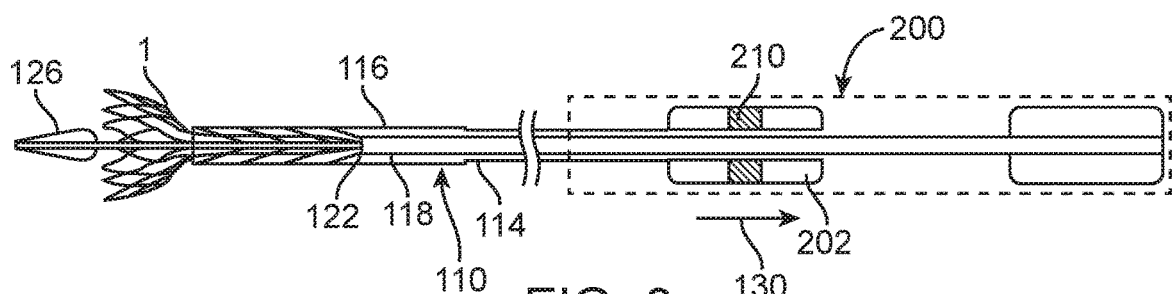
FIG. 3 is a simplified sectional view of a valve prosthesis delivery system according to an aspect of this disclosure.
Figure 4:
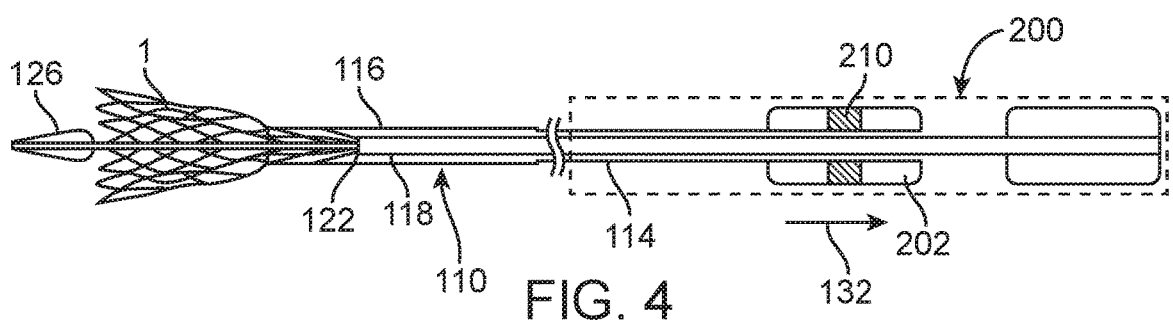
FIG. 4 is a simplified sectional view of a valve prosthesis delivery system according to an aspect of this disclosure.

Once positioning of delivery system 100 is estimated, pusher tube 114 and capsule 116, are partially retracted relative to valve prosthesis 1 as shown in FIG. 3. In particular, a force as indicated by arrow 130 is applied to actuation portion 202 to slide actuation portion 202 toward a proximal end of handle 200. A distal region of valve prosthesis 1 is thus exteriorly exposed relative to capsule 116 and self-expands. In the partially deployed arrangement of FIG. 3, however, at least a proximal region of valve prosthesis 1 remains within an interior area of capsule 116, and thus coupled to delivery system 100. As shown in FIG. 4, further operation of actuation portion 202 due to a force indicated by arrow 132 that moves actuation portion 202 toward a proximal end of handle 200 exposes a larger distal region of valve prosthesis 1 whereas a small proximal region remains within an interior area of capsule 116. In this partially deployed state, a position of valve prosthesis 1 relative to the desired implantation site can again be evaluated.

Figure 5:
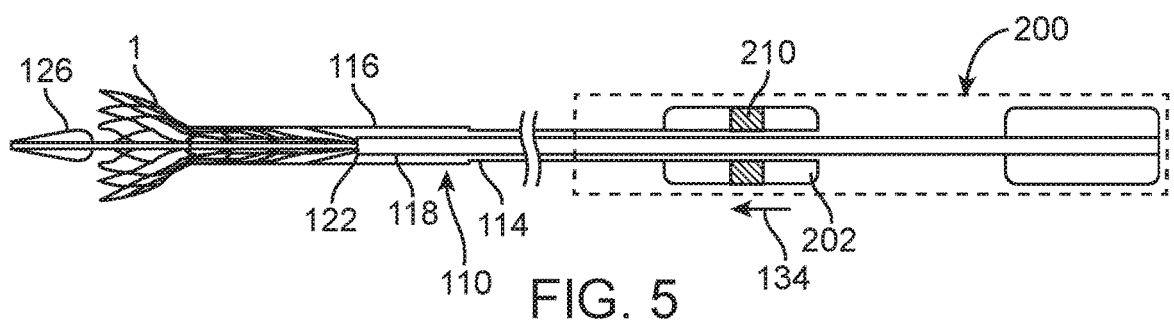
FIG. 5 is a simplified sectional view of a valve prosthesis delivery system according to an aspect of this disclosure.

In the event the clinician believes, based upon the above evaluation, that valve prosthesis 1 should be repositioned relative to the implantation site, valve prosthesis 1 must first be contracted and "resheathed" by transitioning delivery system 100 to a recapturing state. As shown in FIG. 5, oscillating device 210 is activated to induce vibratory motion and actuation portion 202 is moved distally to advance pusher tube 114 and capsule 116 relative to valve prosthesis 1 and central tube 118, as indicated by arrow 134. The vibratory motion created by oscillating device 210 reduces the friction between the outer surface of valve prosthesis 1 and the inner surface of capsule 116. Furthermore, proximal advancement of actuation portion 202 causes capsule 116 to be maneuvered into contact with the exposed distal region of valve prosthesis 1. Thus, capsule 116 readily slides along a surface of valve prosthesis 1.

Figure 6:
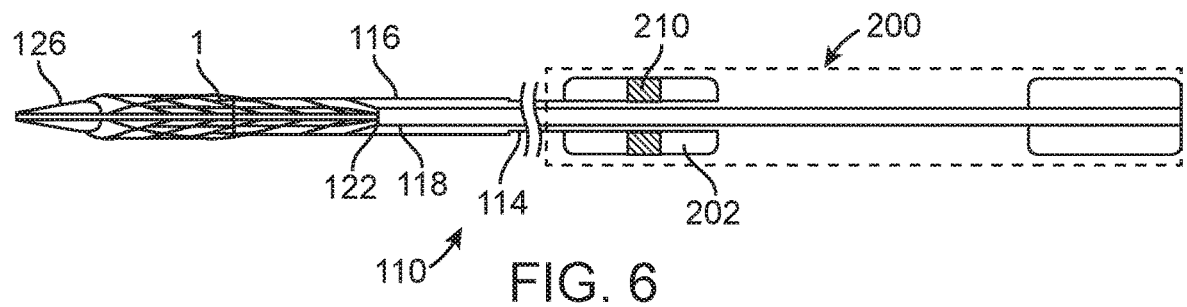
FIG. 6 is a simplified sectional view of a valve prosthesis delivery system according to an aspect of this disclosure.
Figure 7:
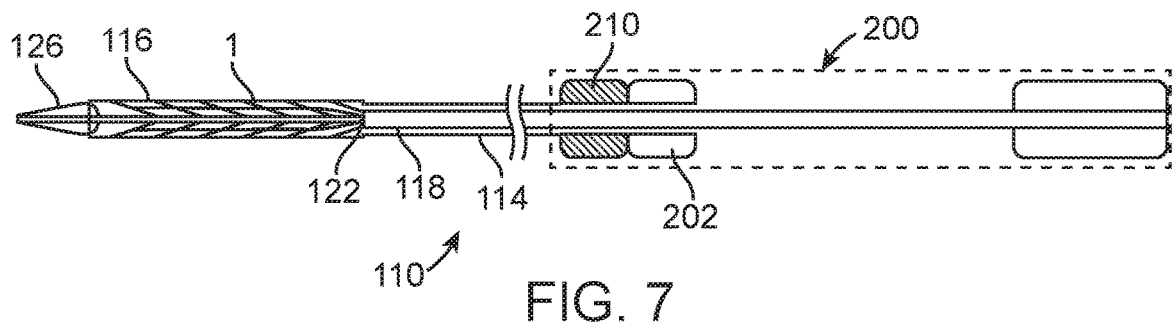
FIG. 7 is a simplified sectional view of a valve prosthesis delivery system according to an aspect of this disclosure.
Figure 8:
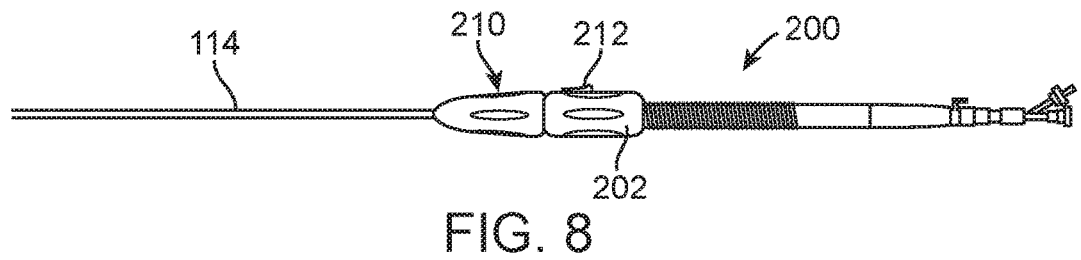
FIG. 8 is a side view of a valve prosthesis delivery system according to an aspect of this disclosure.

Distal advancement of capsule 116 continues until capsule 116 encloses valve prosthesis 1, as shown in FIG. 6. The capsule 116 is distally advanced to a recapturing state, forming an enclosed region that can be repositioned and/or retracted.

Once valve prosthesis 1 is recaptured, delivery system 100 can be repositioned relative to the implantation site, and the process repeated until the clinician is comfortable with the achieved positioning. Alternatively, the reshealthed valve prosthesis 1 can be removed from the patient.

As discussed above, the recapture of valve prosthesis 1 can be facilitated by oscillating device 210. Oscillating device 210 creates vibratory motion between the inner surface of capsule 116 and the outer surface of valve frame 10 in order to reduce the friction between the surfaces and thus reduce the peak force required to recapture a partially deployed valve prosthesis 1.

In one aspect of the invention, oscillating device 210 can transmit vibratory motion to delivery system 100 including catheter assembly 110. In a further aspect, oscillating device 210 can transmit vibratory motion to capsule 116, to valve prosthesis 1, or to both capsule 116 and valve prosthesis 1 in order to reduce the frictional forces between capsule 116 and valve prosthesis 1. Such a reduction in friction between surfaces can be useful, for example, during recapture of valve prosthesis 1. Furthermore, this vibratory motion can reduce the recapture forces exerted on the delivery system during recapture of valve prosthesis 1.

In one aspect, oscillating device 210 can induce a vibratory motion onto delivery system 100 at a frequency that is outside the audible range. For example, oscillating device 210 can induce a vibratory motion at a frequency that is less than or approximately equal to 20 hertz or greater than or approximately equal to 20,000 hertz. In an alternate aspect, oscillating device 210 can induce a vibratory motion onto delivery system 100 at a frequency of approximately 260 hertz. The vibratory motion created by oscillating device 210 can be axial, radial, or a combination of radial and axial motion. In a further aspect of the invention, oscillating device 210 can induce a vibratory motion onto delivery system 100 at the natural frequency of pusher tube 114 and capsule 116. In an alternate aspect, oscillating device 210 can induce a vibratory motion onto delivery system 100 at the natural frequency of central tube 118 and plunger assembly 120.

In one aspect of the invention, oscillating device 210 is positioned on actuation portion 202 on handle 200. In an alternate aspect of the invention, oscillating device 210 can be positioned separate from actuation portion 202, proximal to or distal to actuation portion 202 on handle 200. Oscillation device 210 can also be separate from delivery system 100 as discussed further below. Oscillating device 210 can transmit vibratory motion to pusher tube 114 and capsule 116. In an alternate aspect of the invention, oscillating device 210 can transmit vibratory motion to central tube 118 and plunger assembly 120 including collapsed valve prosthesis 1. In a further aspect, oscillating device 210 can transmit vibratory motion to pusher tube 114, capsule 116, central tube 118 and plunger assembly 120 including collapsed valve prosthesis 1.

Delivery system 100 can also include a generator or other power source (not shown) to supply electricity to oscillating device 210. Oscillating device 210 can also include an activation button 212. Activation button 212 can be a switch or other device to enable oscillating device 210 to begin transmitting vibratory motion during recapture. In one aspect, activation button 212 is positioned on handle 200. For example, activation button 212 can be positioned on oscillating device 210 or on actuation portion 202. In another aspect, activation button 212 can be separate from handle 200 and can be, for example, a foot switch.

In one aspect of the invention, oscillating device 210 can include piezoelectrics. Piezoelectrics are ceramic materials that, by virtue of their crystallographic structure, produce a voltage in response to an applied stress. Conversely, an applied voltage causes a strain within the piezoelectric material. If the electrical input is rapidly alternated, a high-frequency vibration of the piezoelectric material can be created. In one aspect, oscillating device 210 including piezoelectrics, that can be positioned on handle 200 and delivery system 100. In this aspect, vibratory motion is transferred along pusher tube 114 to capsule 116 and/or along central tube 118 to plunger assembly 120 including valve prosthesis 1.

Figure 11:
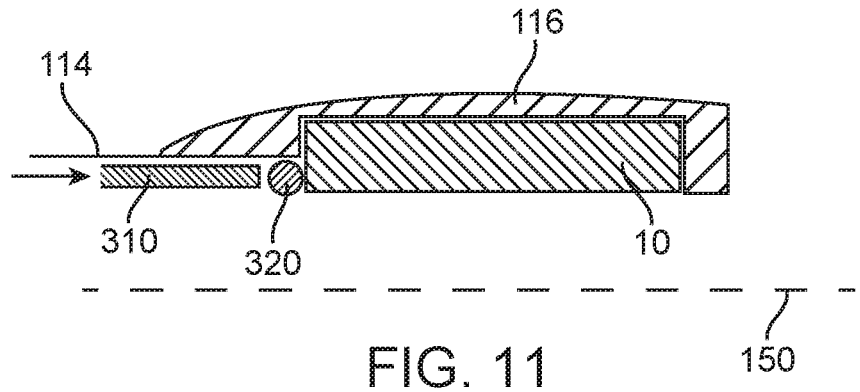
FIG. 11 is a simplified sectional view of a portion of a valve prosthesis delivery system positioned on an axis 150 according to an aspect of this disclosure.
Figure 12:
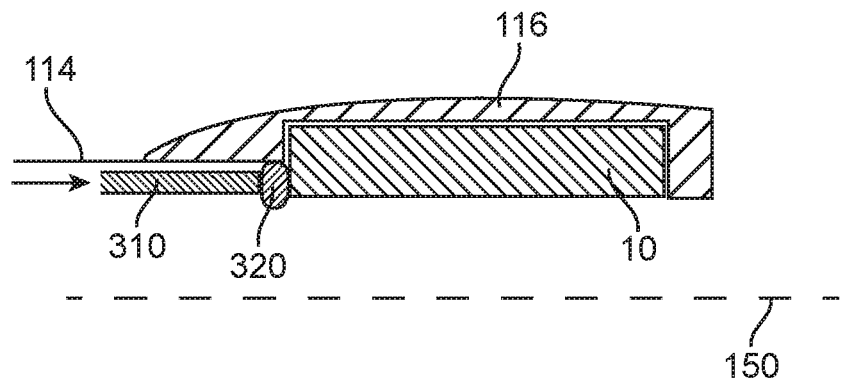
FIG. 12 is a simplified sectional view of a portion of a valve prosthesis delivery system positioned on an axis 150 according to an aspect of this disclosure.

Referring to FIGS. 11-12, delivery system 100 can include an axial pushrod 310 and an annular o-ring 320. In one aspect, axial pushrod 310 is connected to oscillating device 210 positioned on handle 200. Oscillating device 210 transmits alternating axial motion along axial pushrod 310 which in turn compresses and relaxes o-ring 320. This alternating axial motion is converted to alternating radial expansion and contraction of o-ring 320. O-ring 320 transmits radial vibration to capsule 116 as a result of the alternating expansion and contraction of o-ring 320. In an alternate aspect of the invention, o-ring 320 can transmit radial vibration to the portion of frame 10 that remains collapsed within capsule 116 during recapture.

In an alternate aspect of the invention, oscillating device 210 including piezoelectrics can be positioned within or directly adjacent to capsule 116 at a distal end of pusher tube 114. In a further aspect, oscillating device 210 including piezoelectrics can be positioned within or directly adjacent to plunger assembly 120 at a distal end of central tube 118.

In order to supply the necessary voltage to the piezoelectrics in oscillating device 210, delivery system 100 can include a generator or other power source to supply power to oscillating device 210. The generator can send an electrical signal through a conductor (not shown) at a selected amplitude, frequency, and phase to cause the piezoelectrics in oscillating device 210 to expand and contract, thereby converting the electrical energy into mechanical motion. The generator can also include a control system to determine the appropriate amplitude, frequency, and phase. In one aspect of the invention, the piezoelectrics in oscillating device 210 are a piezoelectric bimorph consisting of a piezoelectric layer and a metal layer. An electric field provided by the generator causes one layer to extend and the other layer to contract.

In an alternate aspect of the invention, oscillating device 210 is not positioned on delivery system 100. In this aspect, oscillating device 210 can be an intracardiac catheter or an intravenous ultrasound catheter placed in close proximity to capsule 116 of delivery system 100 during recapture. The intracardiac catheter or intravenous ultrasound catheter can transmit ultrasonic energy at an appropriate frequency in order to induce vibratory motion in capsule 116. Non-limiting examples of intracardiac catheters and intravenous ultrasound catheters useful with systems, devices, and methods of the present disclosure are described in U.S. Pat. Nos. 6,375,615; 6,660,024; 7,637,870 and U.S. Publication No. 2011/0224596, which are incorporated herein by reference in their entirety.

Figure 9:
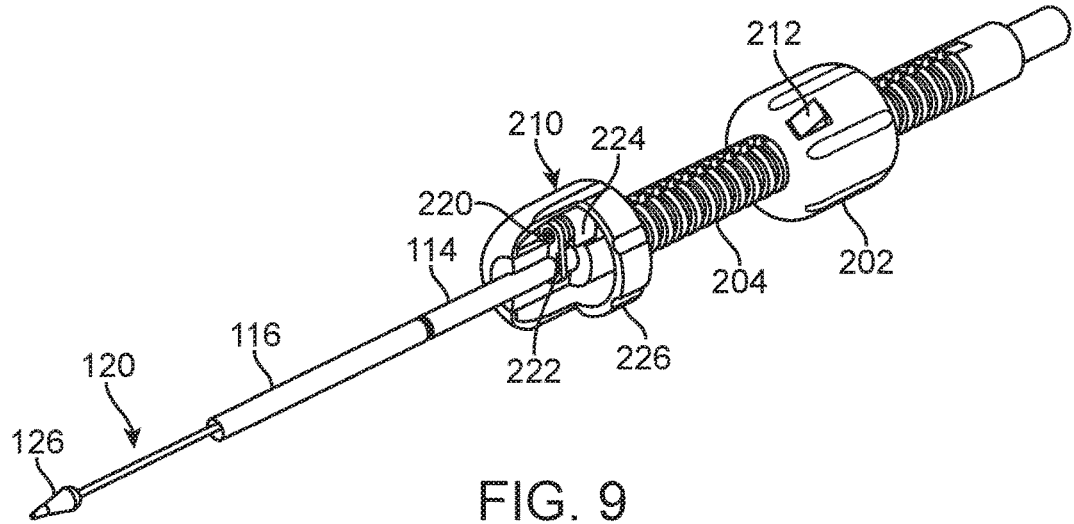
FIG. 9 is a perspective view of a valve prosthesis delivery system according to an aspect of this disclosure.
Figure 10:
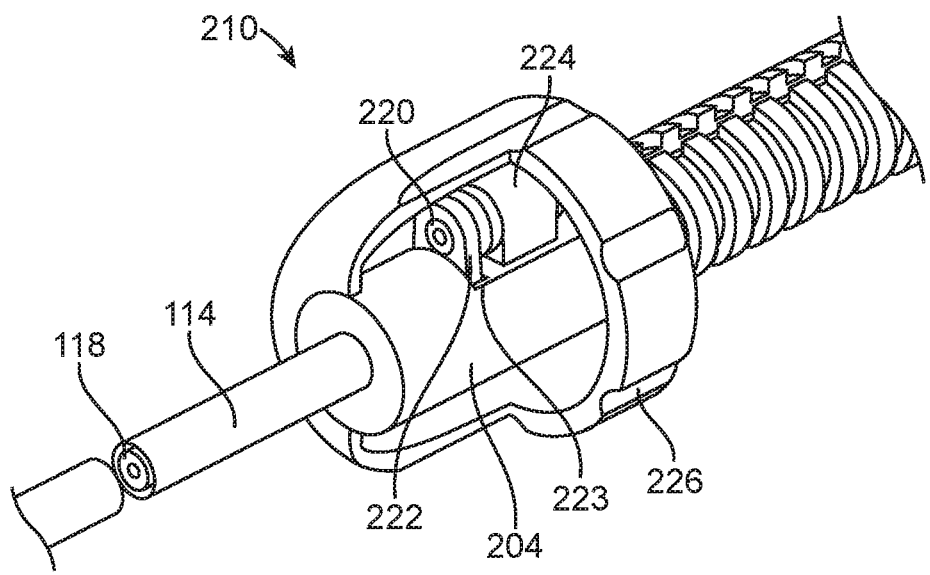
FIG. 10 is a magnified perspective view of a valve prosthesis delivery system according to an aspect of this disclosure.

In an alternate aspect of the invention, oscillating device 210 can induce vibratory motion mechanically. Referring now to FIGS. 9-10, oscillating device 210 can include a motor 224, a cam 220, and a link 222. In this aspect, motor 224 can be connected to handle body 204. In a further aspect, motor 224 can be permanently attached to handle body 204 through screws, adhesive, or other attachment means. Motor 224 is connected to a generator or other power source (not shown) and includes an output shaft connected to cam 220. Cam 220 is connected to link 222 and link 222 is connected to pusher tube 114 or central tube 118. Retaining slot 223 is provided in handle body 204 to allow link 222 to connect to pusher tube 114 or central tube 118. As motor 224 rotates, cam 220 induces motion on link 222 causing link 222 to move up and down within retaining slot 223. Link 222 in turn induces a vibratory motion onto pusher tube 114 and capsule 116. Motor cover 226 surrounds the motor 224, link 222, and cam 220 on handle 200. In one aspect of the invention, actuation portion 202 includes activation button 212 which controls the activation of motor 224. In an alternate aspect of the invention, activation button 212 can be connected to motor cover 226. In a further aspect, motor 224, link 222, and cam 220 are connected to actuation portion 202.

In a further aspect of the invention, oscillating device 210 can induce vibratory motion through magnetism. For example, vibratory motion can be created by rotating a surface having an alternating charge by a stationary magnet. In an alternate aspect, oscillating device 210 can include an electromagnet, a power source, and a magnet assembly to induce vibratory motion onto pusher tube 114 and capsule 116.

Implantation of the valve prosthesis will now be described. As discussed above, the valve prosthesis preferably comprises a self-expanding frame that can be compressed to a contracted delivery configuration onto an inner member of a delivery catheter. This frame design requires a loading system to crimp valve prosthesis 1 to the delivery size, while allowing the proximal end of valve prosthesis 1 to protrude from the loading system so that the proximal end can be attached to attachments 124.

The valve prosthesis and inner member can then be loaded into a delivery sheath of conventional design, e.g., having a diameter of less than 20-24 French.

The delivery catheter and valve prosthesis can then be advanced in a retrograde manner through the femoral artery and into the patient's descending aorta. The catheter then is advanced, under fluoroscopic guidance, over the aortic arch, through the ascending aorta and mid-way across the defective aortic valve. Once positioning of the catheter is confirmed, capsule 116 can be withdrawn proximally, thereby permitting valve prosthesis 1 to self-expand.

As the valve prosthesis expands, it traps the leaflets of the patient's defective aortic valve against the valve annulus, retaining the native valve in a permanently open state. The outflow section of the valve prosthesis expands against and aligns the prosthesis within the ascending aorta, while the inflow section becomes anchored in the aortic annulus of the left ventricle, so that the skirt reduces the risk of perivalvular leaks. As discussed above, recapture of valve prosthesis 1 can be accomplished if necessary.

Alternatively, the valve prosthesis can be delivered through a transapical procedure. In a transapical procedure, a trocar or overtube is inserted into the left ventricle through an incision created in the apex of a patient's heart. A dilator is used to aid in the insertion of the trocar. In this approach, the native valve (e.g. the mitral valve) is approached from the downstream relative to the blood flow. The trocar is retracted sufficiently to release the self-expanding valve prosthesis. The dilator is preferably presented between the valve leaflets. The trocar can be rotated and adjusted as necessary to properly align the valve prosthesis. The dilator is advanced into the left atrium to begin disengaging the proximal section of the valve prosthesis from the dilator.

In an alternate aspect of the invention, the valve prosthesis can be delivered through a transatrial procedure. In this procedure, the dilator and trocar are inserted through an incision made in the wall of the left atrium of the heart. The dilator and trocar are advanced through the native valve and into the left ventricle of heart. The dilator is then withdrawn from the trocar. A guide wire is advanced through the trocar to the point where the valve prosthesis comes to the end of the trocar. The valve prosthesis is advanced sufficiently to release the self-expanding frame from the trocar. The trocar can be rotated and adjusted as necessary to properly align the valve prosthesis. The trocar is completely withdrawn from the heart such that the valve prosthesis self-expands into position and assumes the function of the native valve.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A method of treating a valve disorder in a patient's heart, comprising:

delivering a compressed valve prosthesis attached to a delivery device to an implantation site within a patient, the delivery device including a capsule that compressively contains the valve prosthesis and an oscillator coupled to the capsule;

proximally retracting the capsule relative to the compressed valve prosthesis to expose a region of the valve prosthesis such that the exposed region expands to an uncompressed state;

transmitting vibratory motion to the capsule via the oscillator coupled to the capsule while distally advancing the capsule relative to the valve prosthesis to cause the exposed region of the valve prosthesis to transition toward a compressed arrangement within an interior area of the capsule; and proximally retracting the capsule relative to the compressed valve prosthesis to deploy the valve prosthesis at the implantation site.

2. The method of claim 1, wherein the oscillator comprises piezoelectric material coupled to the capsule, further comprising applying a voltage to the piezoelectric material of the oscillator to induce the vibratory motion.

3. The method of claim 1, wherein the vibratory motion is axial vibratory motion.

4. The method of claim 1, wherein the vibratory motion is radial vibratory motion.

5. The method of claim 1, wherein the vibratory motion is a combination of axial vibratory motion and radial vibratory motion.

6. The method of claim 1, wherein the vibratory motion is at a frequency greater than or equal to 20,000 hertz.

7. The method of claim 1, wherein the vibratory motion is at a frequency less than or equal to 20 hertz.

8. The method of claim 1, wherein the vibratory motion is at a natural frequency of the capsule.

9. The method of claim 1, wherein the capsule includes a flared distal end.

10. A method of delivering a valve prosthesis comprising:
delivering a compressed valve prosthesis attached to a delivery device to an implantation site within a patient, the delivery device including a capsule that compressively contains the valve prosthesis, an inner shaft disposed within the capsule such that the valve prosthesis is disposed on the inner shaft, and an oscillator coupled to a distal end of the inner shaft and configured to transmit vibratory motion to the valve prosthesis;

proximally retracting the capsule relative to the compressed valve prosthesis to expose a region of the valve prosthesis such that the exposed region expands to an uncompressed state; and transmitting a vibratory motion to the valve prosthesis via the oscillator coupled to the inner shaft while distally advancing the capsule relative to the valve prosthesis to cause the exposed region of the valve prosthesis to transition toward a compressed arrangement within an interior area of the capsule.

11. The method of claim 10, further comprising:
repositioning the delivery device;
proximally retracting the capsule relative to the compressed valve prosthesis to deploy the valve prosthesis at the implantation site; and
removing the delivery device from the patient.

12. The method of claim 10, further comprising removing the compressed valve prosthesis and the delivery device from the patient.

13. The method of claim 10, further comprising applying a vibratory motion to the capsule while distally advancing the capsule relative to the valve prosthesis.

14. The method of claim 10, further comprising applying a voltage to a piezoelectric material of the oscillator to induce the vibratory motion.

15. The method of claim 10, wherein the vibratory mothing is at a frequency greater than or equal to 20,000 hertz.

16. The method of claim 10, wherein the vibratory mothing is at a frequency less than or equal to 20 hertz.

17. The method of claim 10, wherein the vibratory motion is axial vibratory motion.

18. The method of claim 10, wherein the vibratory motion is radial vibratory motion.

19. The method of claim 10, wherein the vibratory motion is a combination of radial vibratory motion and axial vibratory motion.

20. The method of claim 10, wherein the vibratory motion is at a natural frequency of the inner shaft.

* * * * *